(12) United States Patent
Luke et al.

(10) Patent No.: US 11,795,084 B2
(45) Date of Patent: Oct. 24, 2023

(54) DENITRIFICATION OF WATER USING BACTERIA

(71) Applicant: NuQuatic, LLC, St. Paul, MN (US)

(72) Inventors: Donald A. Luke, Valrico, FL (US); Ryan Eugene Dickinson, Plant City, FL (US); Janie Michelle Hinson, Lakeland, FL (US)

(73) Assignee: NuQuatic, LLC, St. Paul, MN (US)

( * ) Notice: Subject to any disclaimer, the term of this patent is extended or adjusted under 35 U.S.C. 154(b) by 3 days.

(21) Appl. No.: 17/267,254

(22) PCT Filed: Aug. 21, 2019

(86) PCT No.: PCT/US2019/047524
§ 371 (c)(1),
(2) Date: Feb. 9, 2021

(87) PCT Pub. No.: WO2020/046679
PCT Pub. Date: Mar. 5, 2020

(65) Prior Publication Data
US 2021/0340044 A1    Nov. 4, 2021

Related U.S. Application Data

(60) Provisional application No. 62/724,925, filed on Aug. 30, 2018.

(51) Int. Cl.
*C02F 9/00* (2023.01)
*C12P 3/00* (2006.01)
(Continued)

(52) U.S. Cl.
CPC ............... *C02F 9/00* (2013.01); *C12P 3/00* (2013.01); *C02F 1/20* (2013.01); *C02F 1/70* (2013.01);
(Continued)

(58) Field of Classification Search
CPC ...... C02F 9/00; C02F 1/20; C02F 1/70; C02F 1/727; C02F 1/74; C02F 3/2806;
(Continued)

(56) References Cited

U.S. PATENT DOCUMENTS

| 1,039,325 A | 9/1912 | Schoenherr et al. |
| 4,231,894 A * | 11/1980 | Lavin ...................... C23F 11/08 423/519.2 |

(Continued)

FOREIGN PATENT DOCUMENTS

| CA | 2247871 A1 * | 3/2000 | ................ C02F 3/30 |
| CA | 2673319 A1 * | 1/2011 | ........... A01K 63/045 |

(Continued)

OTHER PUBLICATIONS

Lucy Cook, Brackish_Water_NPL.pdf; https://camblab.info/what-is-brackish-water-and-what-effect-does-a-high-concentration-of-ammonia-have/ (Year: 2012).*

(Continued)

*Primary Examiner* — Ekandra S. Miller-Cruz
(74) *Attorney, Agent, or Firm* — Schwegman Lundberg & Woessner, P.A.

(57) ABSTRACT

Various embodiments relate to denitrification of water using bacteria. A method of denitrification of water includes deoxygenated water including a water-soluble form of nitrogen. The method includes exposing the deoxygenated water to denitrifying bacteria to convert the water-soluble form of nitrogen in the water to nitrogen gas that is removed and to form a denitrified water. The method also includes reoxygenating the denitrified water. Denitrifying bacterial substrates and methods of making the same are also provided.

19 Claims, 1 Drawing Sheet

(51) Int. Cl.
  *C02F 1/20* (2023.01)
  *C02F 1/70* (2023.01)
  *C02F 1/72* (2023.01)
  *C02F 1/74* (2023.01)
  *C02F 3/28* (2023.01)
  *C02F 3/34* (2023.01)
  *C02F 101/10* (2006.01)
  *C02F 101/12* (2006.01)
  *C02F 101/16* (2006.01)
  *C02F 103/00* (2006.01)

(52) U.S. Cl.
  CPC .............. *C02F 1/727* (2013.01); *C02F 1/74* (2013.01); *C02F 3/2806* (2013.01); *C02F 3/34* (2013.01); *C02F 2101/101* (2013.01); *C02F 2101/12* (2013.01); *C02F 2101/163* (2013.01); *C02F 2101/166* (2013.01); *C02F 2103/007* (2013.01); *C02F 2305/06* (2013.01)

(58) Field of Classification Search
  CPC .. C02F 3/34; C02F 2101/101; C02F 2101/12; C02F 2101/163; C02F 2101/166; C02F 2103/007; C02F 2305/06; C02F 1/72; C02F 3/2826; C02F 3/305; C02F 2209/22; C12P 3/00; C12N 11/02; C12N 11/08; C12N 1/20; C12N 11/14
  USPC ....................................................... 210/610
  See application file for complete search history.

(56) References Cited

U.S. PATENT DOCUMENTS

| | | | |
|---|---|---|---|
| 4,970,000 A * | 11/1990 | Eppler | C12N 1/32 210/903 |
| 5,733,455 A | 3/1998 | Molof et al. | |
| 7,384,554 B2 * | 6/2008 | Rittmann | C02F 3/102 210/603 |
| 9,254,582 B2 * | 2/2016 | Luke | C04B 18/023 |
| 9,434,090 B1 * | 9/2016 | Luke | C04B 33/1315 |
| 2001/0045396 A1 | 11/2001 | White | |
| 2005/0109697 A1 | 5/2005 | Olivier | |
| 2005/0133423 A1 * | 6/2005 | Olivier | B01F 25/31243 119/260 |
| 2017/0362108 A1 * | 12/2017 | Huang | C02F 3/305 |
| 2018/0016169 A1 * | 1/2018 | Suzuki | C02F 3/005 |

FOREIGN PATENT DOCUMENTS

| | | | | |
|---|---|---|---|---|
| EP | 0206690 A1 * | 6/1986 | | C02F 1/20 |
| EP | 1531193 A2 * | 5/2005 | | C02F 1/20 |
| WO | WO-2018141071 A1 * | 8/2018 | | B09C 1/00 |
| WO | WO-2020046679 A1 | 3/2020 | | |

OTHER PUBLICATIONS

KR_20110001685_A_M.pdf (Year: 2011).*
KR_20150079378_A_M.pdf (Year: 2015).*
Translation of EP_1531193_A2 (Year: 2005).*
"International Application Serial No. PCT/US2019/047524, International Preliminary Report on Patentability dated Mar. 11, 2021", 9 pgs.
"International Application Serial No. PCT/US2019/047524, International Search Report dated Nov. 13, 2019", 2 pgs.
"International Application Serial No. PCT/US2019/047524, Written Opinion dated Nov. 13, 2019", 7 pgs.
Deng, B., et al., "The Denitrification Characteristics of Pseudomonas stutzeri SC221-M and Its Application to Water Quality Control in Grass Carp Aquaculture", PLoS One 9(12): e114886. Doi:10.1371//journal.pone.0114886;, (Dec. 9, 2014), 16 pgs.
Seelig, B., et al., "Water Quality and nitrogen", North Dakota State University Extension, [Online] Retrieved from the internet: https://www.ag.ndsu.edu/publications/environment-natural-resources/water-quality-and-nitrogen on Oct. 15, 2019, (Jun. 2017), 8 pgs.

* cited by examiner

DENITRIFICATION OF WATER USING BACTERIA

CROSS-REFERENCE TO RELATED APPLICATION

This application is a U.S. National Stage Filing under 35 U.S.C. 371 from International Patent Application Serial No. PCT/US2019/047524, filed Aug. 21, 2019 published as WO 2020/046679 on Mar. 5, 2020, which application claims the benefit of priority to U.S. Provisional Patent Application Serial No. 62/724,925 filed Aug. 30, 2018, the disclosures of which are incorporated herein in their entireties by reference.

BACKGROUND

Nitrogen is a common constituent of agricultural fertilizers, manure, and organic wastes in sewage and industrial effluent. It is an essential element for plant life. However, when there is too much nitrogen in water, it can cause growth of plants and algae and can deplete oxygen from the water at a rate that is greater than ecosystems can handle, causing severe ecological effects including toxic algae blooms, death of native aquatic species, and loss of biodiversity (eutrophication). Simple particulate removal processes such as filtration will remove particulates and lower the total nitrogen concentration; however, these processes will not lower the concentration of water-soluble forms of nitrogen. Although various methods for removal of soluble nitrogen from water are available, these methods are expensive, complex, and difficult to control.

SUMMARY OF THE INVENTION

Various embodiments provide a method of denitrification of water. The method includes deoxygenating water. The water includes a water-soluble form of nitrogen. The method includes exposing the deoxygenated water to denitrifying bacteria to convert the water-soluble form of nitrogen in the water to nitrogen gas that is removed and to form a denitrified water. The method also includes reoxygenating the denitrified water.

Various embodiments provide a method of denitrification of water. The method includes taking water including a soluble form of nitrogen from a source. The water includes a total nitrogen concentration of less than or equal to 20 ppm. The method includes optionally oxidizing or hydrolyzing at least some of the nitrogen to form nitrate. The method includes deoxygenating the water to an oxygen concentration of about 0 ppm to about 0.3 ppm. The method includes exposing the deoxygenated water to denitrifying bacteria immobilized on a porous substrate, to convert nitrate in the water to nitrogen gas that is removed and to form a denitrified water. The method also includes reoxygenating the denitrified water to an oxygen concentration of about 1 ppm to about 20 ppm. The denitrified, reoxygenated water has a total nitrogen concentration that is less than the nitrogen concentration of the water from the source and that is about 0.0 ppm to about 2 ppm total nitrogen.

Various embodiments provide a method of denitrification of water. The method includes taking water from a natural environment, the water including a total nitrogen concentration of greater than 0.8 ppm to equal to or less than or equal to 20 ppm. The method optionally includes oxidizing or hydrolyzing at least some of the nitrogen to form nitrate. The method includes deoxygenating the water to an oxygen concentration of about 0 ppm to about 0.3 ppm. The method includes exposing the deoxygenated water to denitrifying bacteria immobilized on a porous substrate. The immobilized bacteria is cultured from or identical to bacteria native to the area of the natural environment from which the water including nitrogen was taken. Exposing the deoxygenated water to the immobilized denitrifying bacteria converts nitrate in the water to nitrogen gas that is removed and forms a denitrified water. The method also includes reoxygenating the denitrified water to an oxygen concentration of about 1 ppm to about 20 ppm. The denitrified, reoxygenated water has a total nitrogen concentration that is about 0.0 ppm to about 0.8 ppm.

Various embodiments provide a method of immobilizing or maintaining bacteria on a substrate for denitrification of water. The method includes deoxygenating water including a water-soluble form of nitrogen. The method includes exposing the deoxygenated water to denitrifying bacteria on or within a porous substrate to convert the water-soluble form of nitrogen in the water to nitrogen gas that is removed, to grow and maintain the immobilized bacteria on the substrate, and to form a denitrified water.

Various embodiments provide a denitrifying bacterial substrate. The denitrifying bacterial substrate includes a porous substrate. The denitrifying bacterial substrate also includes immobilized bacteria on the porous substrate. The bacteria are cultured from or are identical to anaerobic denitrifying bacteria in the local native environment.

Various embodiments of the denitrifying method, the method of immobilizing or maintaining denitrifying bacteria on a substrate, and of the denitrifying bacterial substrate, have certain advantages over other methods and substrates, at least some of which are unexpected. For example, in various embodiments, the denitrifying substrate and method of using the same can be less expensive, less complex, and easier to control than other denitrification methods and apparatus. Unlike processes relying on a two-stage process using first aerobic bacteria to nitrify or convert nitrogen species to nitrate and nitrite followed by second anaerobic bacteria to denitrify, various embodiments of the present invention accomplish nitrogen removal via a single biological stage.

In various embodiments, the bacteria used in the method and in the denitrifying bacterial substrate are cultured from the local environment or are identical to those found natively in the local environment from which nitrogen is removed from water. Using a local bacteria can avoid introduction of a potentially invasive species of bacteria into the environment.

In various embodiments, a byproduct of the method of denitrification includes at least one of sulfate (e.g., from deoxygenation) and Fe(III) (e.g., from an iron catalyst used for deoxygenation). In various embodiments, sulfate or iron can assist in maintaining bacterial populations at high levels. Sulfate or iron can provide a secondary electron receptor for cellular respiration. By removing dissolved oxygen in the environmental water before passing it through the bacterial substrate, the bacteria is forced to find other electron acceptors, such as nitrate, nitrite, nitric oxide, and nitrous oxide. However, when these nitrogenous electron acceptors are exhausted, the bacteria can utilize the sulfate or Fe(III) as a life-sustaining electron acceptor. By maintaining the denitrifying bacteria using sulfate, the method can remove nitrogen at the same efficiency over long amounts of time with less maintenance than other methods.

In various embodiments, by using high surface area substrate, the denitrifying bacterial substrate can provide a greater rate of nitrogen removal than other nitrogen removal processes. In various embodiments, the high surface area substrate can provide more rapid growth of bacteria and a higher concentration of bacteria than other substrates.

BRIEF DESCRIPTION OF THE FIGURES

The drawings illustrate generally, by way of example, but not by way of limitation, various embodiments of the present invention.

DETAILED DESCRIPTION OF THE INVENTION

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range. The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt %/o or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

In various embodiments, salts having a positively charged counterion can include any suitable positively charged counterion. For example, the counterion can be ammonium ($NH_4^+$), or an alkali metal such as sodium ($Na^+$), potassium ($K^+$), or lithium ($Li^+$). In some embodiments, the counterion can have a positive charge greater than +1, which can in some embodiments complex to multiple ionized groups, such as $Zn^{2+}$, $Al^{3+}$, or alkaline earth metals such as $Ca^{2+}$ or $Mg^{2+}$.

Concentrations referred to herein are by weight unless indicated otherwise.

Method of Denitrification of Water.

Various embodiments provide a method of denitrification of water. The method can include deoxygenating water that includes a water-soluble form of nitrogen. The method can include exposing the deoxygenated water to denitrifying bacteria to convert the water-soluble form of nitrogen in the water to nitrogen gas that is removed and to form a denitrified water. The method can optionally include reoxygenating the denitrified water; in some embodiments, reoxygenating is performed, while in other embodiments, the method is free of the reoxygenating. The method can be a continuous process, a batch-wise process, or any combination thereof (e.g., having some steps continuous and other steps batch-wise).

The water including the water-soluble form of the nitrogen, or an unoxidized or unhydrolyzed precursor thereof, can be taken or derived from a natural or non-natural source. The method can be a method of denitrification of natural water, denitrification of waste water, or for denitrification of drinking water. The water can be taken from a natural source of water in the environment, such as a pond, lake, river, stream, and the like. Naturally sourced water can include water-soluble forms of nitrogen, water-insoluble forms of nitrogen, or a combination thereof. The water can optionally be filtered prior to deoxygenation, which can remove some or substantially all water-insoluble forms of nitrogen, either prior to or during the onset of the method. The water-soluble form of nitrogen can be or can include nitrate ($NO_3^-$), nitrite ($NO_2^-$), nitric oxide (NO), nitrous oxide ($N_2O$), nitrogen gas ($N_2$), or a combination thereof.

The water including the water-soluble form of nitrogen that is denitrified can have any suitable nitrogen concentration before deoxygenation and at the time of exposure to the bacteria for denitrification. For example, the water including the water-soluble form of nitrogen can have a nitrogen concentration of about 0.1 ppm to about 10 ppm total nitrogen, or about 1 ppm to about 4 ppm total nitrogen, or about 0.1 ppm or less, or less than, equal to, or greater than about 0.2, 0.4, 0.6, 0.8, 1, 1.2, 1.4, 1.6, 1.8, 2, 2.2, 2.4, 2.6, 2.8, 3, 3.2, 3.4, 3.6, 3.8, 4, 4.5, 5, 6, 7, 8, 9, or about 10 ppm or more total nitrogen. As used herein, "total nitrogen" means the sum of ammonia, organic nitrogen, reduced nitrogen, nitrate nitrogen, and nitrite nitrogen. The water including the water-soluble form of nitrogen can have a nitrate concentration of about 0.01 ppm to about 10 ppm, or about 1 ppm to about 3 ppm, or about 0.01 ppm or less, or less than, equal to, or greater than about 0.2, 0.4, 0.6, 0.8, 1, 1.2, 1.4, 1.6, 1.8, 2, 2.2, 2.4, 2.6, 2.8, 3, 3.2, 3.4, 3.6, 3.8, 4, 4.5, 5, 6, 7, 8, 9, or about 10 ppm or more.

The method can further include, prior to the deoxygenation, optionally subjecting water including nitrogen to an oxidation or hydrolysis step (e.g., water including an unoxidized or unhydrolyzed precursor of the water-soluble form of nitrogen), such as water taken from a natural source of water, to provide the water including the water-soluble form of nitrogen. The oxidation or hydrolysis step can convert at least some nitrogen into water-soluble forms of nitrogen such as nitrate. The oxidation or hydrolysis can include any suitable conditions that convert at least some of the nitrogen into water-soluble forms of nitrogen, such as treatment with acid, base, ferrate, ozone, ferric chloride, potassium permanganate, potassium dichromate, potassium chlorate, potassium persulfate, sodium persulfate, perchloric acid, peracetic acid, potassium monopersulfate, hydrogen peroxide, sodium hypochlorite, potassium hypochlorite, or a combination thereof. The oxidation or hydrolysis can be performed for any suitable period of time and at any suitable temperature such that the oxidized and water-soluble form of nitrogen is formed. The oxidation or hydrolysis be performed for about 1 s to about 24 h, or about 10 s to about 8 h, or about 1 min to about 60 min, or about 5 min to about 15 min, or about 1 s or less, or less than, equal to, or greater than about 10 s, 30 s, 1 min, 5, 10, 15, 20, 30, 40, 50 min, 1 h, 2, 3, 4, 5, 6, 7, 8, 9, 10, 12, 14, 16, 18, 20, 22, or about 24 h or more. The oxidation or hydrolysis can be performed at a temperature of about greater than 0° C. to less than or equal to about 200° C., or about 1° C. to about 100° C., or about 15° C. to about 30° C., or about 1° C. or less, or less than, equal to, or greater than about 5° C., 10, 15, 20, 30, 40, 50, 60, 70, 80, 90, 95, 100, 110, 120, 150, or about 200° C. or more.

The water including nitrogen, or the water including a water-soluble form of nitrogen, can have any suitable oxygen concentration prior to the deoxygenation, such as about 0 ppm to about 20 ppm oxygen, or about 2 ppm to about 8 ppm, or about 0, or less than, equal to, or greater than about 0.5, 1, 1.5, 2, 2.5, 3, 3.5, 4, 4.5, 5, 5.5, 6, 6.5, 7, 7.5, 8, 9, 10, 11, 12, 13, 14, 15, 16, 18, or about 20 ppm or more.

Deoxygenation.

The method can include deoxygenating water that includes a water-soluble form of nitrogen, which can be water including nitrogen that is taken from a suitable source, such as a natural or non-natural source. The method can be a method of denitrification of natural water, denitrification of waste water, or for denitrification of drinking water. The water can be optionally filtered, and optionally subjected to an oxidation or hydrolysis to convert some of the nitrogen into water-soluble forms of nitrogen. The deoxygenation prepares the water for exposure to the denitrification bacteria. The water can optionally be filtered prior to the deoxygenating, which can remove at least some or substantially all water-insoluble forms of nitrogen from the water.

The deoxygenation can include any suitable method of decreasing the oxygen concentration to sufficient levels for the method to be performed as described herein, such as including treating with one or more deoxygenating compounds, sulfite compounds, catalysts, heating, exposing to reduced pressure, sparging with a stripping gas (e.g., an inert gas like nitrogen), sonicating, contacting with a membrane contactor, or a combination thereof. The deoxygenated water can have any suitable oxygen concentration, such as about 0 ppm to about 2 ppm, or about 0 ppm to about 0.3 ppm, or about 0 ppm, or less then, equal to, or greater than about 0.01, 0.02, 0.04, 0.06, 0.08, 0.1, 0.12, 0.14, 0.16, 0.18, 0.2, 0.22, 0.24, 0.26, 0.28, 0.3, 0.32, 0.34, 0.36, 0.38, 0.4, 0.45, 0.5, 0.55, 0.6, 0.7, 0.8, 0.9, 1.0, 1.1, 1.2, 1.3, 1.4, 1.5, 1.6, 1.7, 1.8, 1.9, or about 2 ppm or more. The deoxygenating can remove any suitable overall proportion of the oxygen to reach the desired oxygen concentration, such as about 0.01% to about 100%, or about 50% to about 99.999%, or about 0.01% or less, or less than, equal to, or greater than about 0.1%, 0.5, 1, 2, 3, 4, 6, 8, 10, 15, 20, 25, 30, 40, 50, 55, 60, 65, 70, 75, 80, 82, 84, 86, 88, 90, 91, 92, 93, 94, 95, 96, 97, 98, 99, 99.9, 99.99, or about 99.999% or more. The deoxygenating can be performed for any suitable amount of time, such as about 1 second to about 1 day, or about 1 minute to about 30 minutes, or about 1 s or less, or less than, equal to, or greater than about 10 s, 30 s, 1 min, 5, 10, 15, 20, 30, 40, 50 min, 1 h, 2, 3, 4, 5, 6, 7, 8, 9, 10, 12, 14, 16, 18, 20, 22, or about 24 h or more.

The deoxygenating can include exposing the water including the water-soluble form of nitrogen to one or more sulfite compounds in the presence of a metal catalyst. The one or more sulfite compounds can be in solid or liquid form and can include sodium sulfite, potassium sulfite, sodium bisulfite, sodium metabifsulfite, potassium bisulfite, potassium metabisulfite, or a combination thereof. The one or more sulfite compounds can be used at any effective concentration, such as about 10 ppb to about 10,000 ppb, or about 100 ppb to about 250 ppb, or about 10 ppb or less, or less than, equal to, or greater than about 20 ppb, 30, 40, 50, 60, 80, 100, 120, 140, 160, 180, 200, 220, 240, 250, 300, 400, 500, 600, 800, 1,000, 1,500, 2,000, 2,500, 3,000, 4,000, 5,000, 6,000, 8,000, or about 10,000 ppb or more. The one or more sulfites can be added in any suitable amount based on the amount of oxygen present, such as in an amount of about 1 ppm to about 10,000 ppm per 1 ppm dissolved oxygen, or about 5 ppm to about 25 ppm, or about 1 ppm or less, or less than, equal to, or greater than about 2 ppm, 3, 4, 5, 6, 8, 10, 15, 20, 30, 40, 50, 60, 80, 100, 120, 140, 160, 180, 200, 220, 240, 250, 300, 400, 500, 600, 800, 1,000, 1,500, 2,000, 2,500, 3,000, 4,000, 5,000, 6,000, 8,000, or about 10,000 ppm or more, per 1 ppm dissolved oxygen.

The metal catalyst can be a homogeneous catalyst or a heterogeneous catalyst and can include iron, copper, cobalt, a platinum group metal, or a combination thereof. The metal catalyst can include an iron catalyst. The metal catalyst can be used at any effective concentration, such as about 10 ppb to about 10,000 ppb, or about 400 ppb to about 1,000 ppb, or about 10 ppb or less, or less than, equal to, or greater than about 20, 30, 40, 50, 60, 80, 100, 120, 140, 160, 180, 200, 220, 240, 250, 300, 400, 500, 600, 700, 800, 900, 1,000, 1,500, 2,000, 2,500, 3,000, 4,000, 5,000, 6,000, 8,000, or about 10,000 ppb or more. Each liter of the deoxygenated water can be exposed to an effective amount of the metal catalyst, such as about 0.1 mg to about 100 mg of the metal catalyst, in combination with the one or more sulfites, or about 0.1 mg or less, or less than, equal to, or greater than about 0.2, 0.4, 0.6, 0.8, 1, 2, 3, 4, 5, 6, 8, 10, 15, 20, 30, 40, 50, 60, 80, or about 100 mg or more.

Denitrification.

The method can include exposing the deoxygenated water to denitrifying bacteria to convert the water-soluble form of nitrogen in the water to nitrogen gas that is removed and to form a denitrified water.

The method can effectively denitrify the water, providing a denitrified and optionally reoxygenated water that can have any suitable nitrogen concentration due to denitrification from the denitrifying bacteria. For example, the denitrified and optionally reoxygenated water can have a nitrogen concentration of about 0.0 ppm to about 2 ppm total nitrogen, or about 0.5 ppm to about 0.8 ppm total nitrogen, or 0 ppm, or less than, equal to, or greater than about 0.01, 0.05, 0.1, 0.15, 0.2, 0.25, 0.3, 0.35, 0.4, 0.45, 0.5, 0.52, 0.54, 0.56, 0.58, 0.6, 0.62, 0.64, 0.66, 0.68, 0.7, 0.72, 0.74, 0.76, 0.78, 0.8, 0.85, 0.9, 0.95, 1, 1.1, 1.2, 1.3, 1.4, 1.5, 1.6, 1.7, 1.8, 1.9, or about 2 ppm or more total nitrogen. The denitrified and optionally reoxygenated water can have a total nitrogen concentration that is about 0% to about 70% of the total nitrogen concentration of the water including the water-soluble form of nitrogen, or about 20% to about 60%, or about 0%, or less than, equal to, or greater than about 5%, 10, 15, 20, 22, 24, 26, 28, 30, 32, 34, 36, 38, 40, 42, 44, 46, 48, 50, 52, 54, 56, 58, 60, 65, or about 70% or more of the total nitrogen concentration of the water including the water-soluble form of nitrogen. The denitrified and optionally reoxygenated water can have a nitrate concentration that is about 0.0 ppm to about 2 ppm, or about 0.0 ppm to about 0.8 ppm, or about 0 ppm, or less than, equal to, or greater than about 0.01, 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or about 2 or more. The denitrified and optionally reoxygenated water has a nitrate concentration that is about 0% to about 70% of the nitrate concentration of the water including the water-soluble form of nitrogen, or about 0% to about 600%, or about 0%, or less than, equal to, or greater than about 5%, 10, 15, 20, 25, 30, 35, 40, 45, 50, 55, 60, 65, or about 70% or more of the nitrate concentration of the water including the water-soluble form of nitrogen.

The method can include adding nutrients, food, or a combination thereof, to the water. In other embodiments, no nutrients or food are added during the method. Prior to addition of nutrients or food, the water may naturally contain some amount of nutrients or food, or the water can be substantially free of nutrients of food. Prior to addition of nutrients or food, the water can optionally be filtered, or the water can be free of filtration. Nutrients or food can be added at any suitable part of the method, such as prior to the denitrification, during the denitrification, or a combination thereof. The nutrients or food can be added prior to the deoxygenating, during the deoxygenating, after the deoxygenating, or a combination thereof. The nutrients can be any suitable nutrients that allow the bacteria to grow or be maintained. The nutrients can include compounds including nitrogen, sulfur, phosphorus, potassium, iron, molybdenum, tungsten, magnesium, calcium, sodium, copper, or a combination thereof, such as in the form of elemental materials, or compounds thereof such as ionic compounds (e.g, salts) or as complexes (e.g., with ligands). The nutrients can include iron chloride.

The denitrifying bacteria can 1) reduce nitrate ($NO_3^-$) to nitrite ($NO_2^-$), 2) reduce nitrite ($NO_2^-$) to nitric oxide (NO), 3) reduce nitric oxide (NO) to nitrous oxide ($N_2O$), and 4) reduce nitrous oxide ($N_2O$) to nitrogen gas ($N_2$). Nutrients can be added to cause the soluble nitrogen to be converted to nitrogen gas.

The food and nutrients can be added to maintain a concentration of molybdenum in the deoxygenated water fed to the denitrifying bacteria of 0.01 ppb to about 100 ppb, or about 0.1 ppb to about 20 ppb, or about 0.01 ppb or less, or less than, equal to, or greater than about 0.05, 0.1, 0.2, 0.4, 0.6, 0.8, 1, 1.5, 2, 2.5, 5, 10, 15, 20, 25, 50, 75, or about 100 ppb or more. Nitrate can be reduced to nitrite within the bacteria which can be catalyzed by nitrate reductase and which can experience feedback inhibition from nitrite buildup. Bacterial production of nitrate reductase requires sufficient levels of molybdenum in solution and is competitively inhibited by tungsten. In some embodiments, in order to facilitate this step, tungsten can be reduced in concentration and/or molybdenum levels can be increased to outcompete tungsten. In order to prevent negative feedback inhibition by nitrite buildup, the step of reduction of nitrite ($NO_2^-$) to nitric oxide (NO) should occur at a similar rate.

The food and nutrients can be added to maintain a concentration of the combination of iron and copper in the deoxygenated water fed to the denitrifying bacteria of about 50 ppb to about 10,000 ppb, or about 200 ppb to about 2,000 ppb, or about 50 ppb or less, or less than, equal to, or greater than about 100 ppb, 150, 200, 250, 300, 400, 500, 750, 1,000, 1,250, 1,500, 1,750, 2,000, 2,500, 5,000, 7,500, or about 10,000 ppb or more. Nitrite can be reduced to nitric oxide within the bacteria, which can be catalyzed by nitrite reductase, and which can experience negative feedback inhibition from nitric oxide buildup. Bacterial production of nitrite reductase requires sufficient levels of iron and/or copper in solution. In order to prevent negative feedback inhibition from nitric oxide buildup, the step of reduction of nitric oxide (NO) to nitrous oxide ($N_2O$) must should occur at a similar rate.

The food and nutrients can be added to maintain a concentration of iron in the deoxygenated water fed to the denitrifying bacteria of about 25 ppb to about 5,000 ppb, or about 100 ppb to about 1,000 ppb, or about 25 ppb or less, or less than, equal to, or greater than about 50 ppb, 100, 150, 200, 250, 300, 400, 500, 600, 800, 1,000, 1,500, 2,000, 2,500, 3,000, 4,000, or about 5,000 ppb or more. Nitric oxide can be reduced to nitrous oxide within the bacteria, which can be catalyzed by nitric oxide reductase and which can experience negative feedback inhibition from nitrous oxide buildup. Bacterial production of nitric oxide reductase requires sufficient levels of iron in solution. In order to prevent negative feedback inhibition from nitrous oxide buildup, the reduction of nitrous oxide ($N_2O$) to nitrogen gas ($N_2$) should occur at a similar rate.

The food and nutrients are added to maintain a concentration of copper in the deoxygenated water fed to the denitrifying bacteria of about 25 ppb to about 5,000 ppb, or about 100 ppb to about 1,000 ppb, or about 25 ppb or less, or less than, equal to, or greater than about 50 ppb, 100, 150, 200, 250, 300, 400, 500, 600, 800, 1,000, 1,500, 2,000, 2,500, 3,000, 4,000, or about 5,000 ppb or more. Nitrous oxide can be reduced to nitrogen gas within the bacteria, catalyzed by nitrous oxide reductase. Bacterial production of nitrous oxide reductase requires sufficient levels of copper in solution.

The food can be any suitable food that allows the bacteria to grow or be maintained. The food can include a carbon source, such as any organic source of carbon, such as a plant product, a bacterial product, a fungal product, an animal product, or a combination thereof. The carbon source can include sucrose, citric acid, cellulose fibers, wood chips, saw dust, or a combination thereof. The carbon source can be sucrose, such as at a concentration of about 1 ppm to about 100,000 ppm, or about 50 ppm to about 500 ppm, or about 50 ppm to about 150 ppm, or about 1 ppm or less, or less than, equal to, or greater than about 25 ppm, 50, 75, 100, 150, 200, 250, 300, 400, 500, 750, 1,000, 2,000, 5,000, 10,000, 20,000, 50,000, 75,000, or about 100,000 ppm or more.

The nutrients and food can be added in an amount such that the carbon to nitrate ratio allows the bacteria to grow or be maintained, such as a carbon to nitrate ratio of about 0.01 mg carbon to about 1 g carbon per 1 mg nitrate, or about 1 mg carbon to about 5 mg carbon per 1 mg nitrate, or about 0.01 g carbon or less, or less than, equal to, or greater than 0.05 mg, 0.1 mg, 0.2, 0.4, 0.6, 0.8, 1, 1.5, 2, 2.5, 3, 3.5, 4, 4.5, 5, 6, 8, 10, 15, 20, 25, 50, 75, 100, 125, 150, 200, 250, 500, 750 mg carbon, or about 1 g carbon or more per 1 mg nitrate.

The denitrifying bacteria can be in any suitable form during contacting with the water including the water-soluble form of nitrogen. For example, the denitrifying bacteria can be in solution (e.g., as a suspension), immobilized, or a combination thereof.

The denitrifying bacteria can be indigenous to soil in the location of a natural source from which the water including the nitrogen was taken. The denitrifying bacteria can be cultured from bacteria taken from soil in the natural location of the water containing the water-soluble form of nitrogen, or the denitrifying bacteria can be cultured from bacteria taken from a different location than the natural source of the water but can be the same as bacteria that is indigenous to bacteria in the location of the natural source of the water containing the nitrogen. Various embodiments provide culturing of local natural denitrifying bacteria for utilization as a feedstock for initial denitrifying bacteria culture establishment and to replace bacterial losses. The denitrifying bacteria can be cultured from or identical to bacteria at the shore of the natural location of the water containing the nitrogen used in the method or to which the denitrified water is returned or a combination thereof, or within about 0.001 miles to about 100 miles, or about 0.1 miles to about 5 miles, or about 0.001 miles or less, or 0.005, 0.01, 0.05, 0.1, 0.5, 1, 2, 3, 4, 5, 6, 8, 10, 15, 20, 25, 30, 40, 50, 60, 70, 80, 90, or about 100 miles or more.

The denitrifying bacteria can be any suitable denitrifying bacteria that can be used to perform the method described herein. The denitrifying bacteria can include anaerobic denitrifying bacteria, aerobic denitrifying bacteria, or a combination thereof. Anaerobic denitrifying bacteria can form the majority of or substantially all of the denitrifying bacteria. The denitrifying bacteria can transform nitrate in the deoxygenated water into nitrogen gas, which can bubble out of the water. Nitrate can be transformed to nitrogen gas via any suitable mechanism. For example, the denitrifying bacteria can reduce nitrate ($NO_3^-$) to nitrite ($NO_2^-$), reduce nitrite ($NO_2^-$) to nitric oxide (NO), reduce nitric oxide (NO) to nitrous oxide ($N_2O$), reduce nitrous oxide ($N_2O$) to nitrogen gas ($N_2$), or a combination thereof. The denitrifying bacteria can include *Thiobacillus denitrificans*, *Micrococcus denitrificans*, a *Serratia*, a *Pseudomonas*, an *Achromobacter*, a *alkaligenes*, a *bacillus*, or a combination thereof. The denitrifying bacteria can include a *Pseudomonas*, such as *Pseudomonas stutzeri*, *Pseudomonas denitrificans*, *Pseudomonas aeruginosa*, and combinations thereof.

The method can include culturing the bacteria on a medium (e.g., agar) at any suitable stage of the process to verify or identify the species present, to measure bacterial population, growth rate, or a combination thereof. The method can include maintaining a culture of the bacteria.

The method can include reducing or minimizing the formation of hydrogen sulfide by removing the water from the denitrifying bacteria once the water-soluble form of nitrogen is substantially completely transformed into nitrogen gas. In some embodiments, once the denitrifying bacteria reduces substantially all the nitrogen compounds to nitrogen gas, the bacteria begin reducing sulfate, such as from the deoxygenation, into hydrogen sulfide. Sulfate as a secondary electron receptor can be beneficial to maintaining the maximum population of bacteria; however, hydrogen sulfide is corrosive, hazardous, and excessive production increases post treatment costs, so production can be kept at a minimum through proper sulfite dosing or minimizing residence time of the water with the bacteria.

The method can include recirculating the denitrified water back into the process before or after the deoxygenation. For example, the denitrified water can be recirculated back into contact with the bacteria before or after the nutrient and food addition, or the denitrified water can be reoxygenated and can be recirculated back to the deoxygenation step.

The method can include filtering the denitrified water. For example, the filtration can remove some or all bacteria that may elute with the water.

Reoxygenation.

The method can optionally include reoxygenating the denitrified water; in some embodiments, reoxygenating is performed, while in other embodiments, the method is free of the reoxygenating. The reoxygenating can bring oxygen levels to suitable levels for release back into the environment.

The reoxygenating can be performed in any suitable way. For example, chemical (e.g., hydrogen peroxide) or physical treatments (e.g., gas sparging) can be used. In some embodiments, the reoxygenating includes aerating the denitrified water or sparging of oxygen-containing gas into the denitrified water. The reoxygenating can include sparging air into the denitrified water, such as via an air bubbler.

The reoxygenated water can have any suitable oxygen concentration, such as about 1 ppm to about 20 ppm, or about 2 ppm to about 8 ppm, or about 1 or less, or less than, equal to, or greater than about 1.5, 2, 2.5, 3, 3.5, 4, 4.5, 5, 5.5, 6, 6.5, 7, 7.5, 8, 9, 10, 11, 12, 13, 14, 15, 16, 18, or about 20 ppm or more. Prior to reoxygenation, the water can have any suitable proportion of the oxygen concentration achieved by reoxygenation, such as about 0.001% to about 99.99%, or about 50% to about 99.9%, or about 0.001% or less, or less than, equal to, or greater than about 0.01%, 0.1, 0.5, 1, 2, 4, 6, 8, 10, 15, 20, 25, 30, 40, 50, 55, 60, 65, 70, 75, 80, 82, 84, 86, 88, 90, 91, 92, 93, 94, 95, 96, 97, 98, 99, 99.9, or about 99.99% or more.

The method can further include adjusting the pH of the reoxygenated water. For example, acid or base addition can be used to bring the pH of the reoxygenated water to about 6 to about 8, or to about 7.

The method can further include removing or reducing the concentration of one or more gases in the reoxygenated water if present in unsuitable high concentrations, such as concentrations above regulated limits. For example, the method can include scrubbing from the reoxygenated water hydrogen sulfide, nitrous oxide, nitric oxide, or a combination thereof, such as if present in concentrations above regulated limits.

The method can optionally include filtering the reoxygenated water. The method can include returning the denitrified and reoxygenated water to the natural environment, as to a natural source from which the water including nitrogen water was taken. The method can include returning the denitrified and reoxygenated water to the natural environment downstream of the origin of the water including the water-soluble form of nitrogen, or an unoxidized or unhydrolyzed precursor thereof.

Bacteria Immobilized on a Substrate.

The denitrifying bacteria can be an immobilized denitrifying bacteria, such as immobilized in or on an inorganic material, a natural polymer (e.g., alginate, carrageenan, chitosan, chitin, collagen, gelatin, cellulose, starch, pectin, sepharose, or a combination thereof), a synthetic polymer, a porous substrate, an aerogel (e.g., silica, carbon, or metal oxide), a matrix (e.g., a three-dimensional molecular framework that holds the bacteria in place but allows water to circulate into contact with the bacteria), fibers, or a combination thereof.

In some embodiments, the denitrifying bacteria can be immobilized on a porous substrate, which can serve as a surface for the bacteria to grow and be maintained as well as for the bacteria to come into contact with the water and perform denitrification. The immobilization can be a passive immobilization, such that the bacteria are not encapsulated but are rather living on the surface of the substrate.

The porous substrate can be any suitable porous substrate that can allow for growth, maintenance, and denitrification of water by the bacteria. The porous substrate can include a synthetic substrate, a natural substrate, a ceramic, a metal, a clay, a polymer, a natural mineral, rock, activated carbon, zeolite, cement, a ceramic foam, diatomaceous earth, silica, glass, charcoal, or a combination thereof.

The porous substrate can include a ceramic and a reactive calcium available to form a solid calcium salt with an anionic material. The porous substrate can be a vitrified mixture of a non-clumping clay, dolomitic limestone, CaO, and peat. In some embodiments, about 50 wt % to about 80 wt % of the vitrified mixture is the non-clumping clay, such as about 50 wt % or less, or less than, equal to, or greater than about 52 wt %, 54, 56, 58, 60, 62, 64, 66, 68, 70, 72, 74, 76, 78, or about 80 wt % or more. In some embodiments, about 5 wt % to about 20 wt % of the vitrified mixture is dolomitic limestone (e.g., less than, equal to, or greater than about 5, 6, 7, 8, 9, 10, 11, 12, 13, 14, 15, 16, 17, 18, 19, or about 20 wt %), such that about 0.1 wt % to about 5 wt % of the vitrified mixture is magnesium, such as about 0.1 wt % or less, or less than, equal to, or greater than about 0.2, 0.4, 0.6, 0.8, 1, 1.5, 2, 2.5, 3, 3.5, 4, 4.5, or about 5 wt % or more. In some embodiments, about 0.1 wt % to about 10 wt % of the vitrified mixture is $CaCO_3$, such as about 0.1 wt % or less, or less than, equal to, or greater than about 0.2, 0.4, 0.6, 0.8, 1, 1.5, 2, 2.5, 3, 3.5, 4, 4.5, 5, 6, 7, 8, 9, or about 10 wt % or more. In some embodiments, about 0.01 wt % to about 5 wt % of the vitrified mixture is CaO, such as about 0.01 wt %/o or less, or less than, equal to, or greater than about 0.05, 0.1, 0.2, 0.4, 0.6, 0.8, 1, 1.5, 2, 2.5, 3, 3.5, 4, 4.5, or about 5 wt % or more. In some embodiments, about 1 wt % to about 20 wt % of the vitrified mixture is peat, such as about 1 wt % or less, or less than, equal to, or greater than about 2, 4, 6, 8, 10, 12, 14, 16, 18, or about 20 wt % or more. In some embodiments, about 0 wt % to about 30 wt % of the vitrified mixture is water, such as about 0 wt %, or less than, equal to, or greater than about 0.01 wt %, 0.1, 0.5, 1, 2, 4, 6, 8, 10, 12, 14, 16, 18, 20, 25, or about 30 wt % or more. In some embodiments, the porous substrate is identical to that described in U.S. Provisional Application No. 62/566,858, and in U.S. Pat. Nos. 6,627,083, 9,254,582, and 9,434,090, the contents of which are hereby incorporated by reference.

During the denitrifying, the deoxygenated water is flowed through and past the denitrifying bacteria immobilized on the porous substrate at a suitable flow rate, such as a flow rate of 0.001 gallons per minute per cubic foot of ceramic substrate to 5 gallons per minute per cubic foot of ceramic substrate, or about 0.04 gallons per minute per cubic foot of ceramic substrate to 0.26 gallons per minute per cubic foot of ceramic substrate, or about 0.001 or less, or less than, equal to, or greater than about 0.005, 0.01, 0.05, 0.1, 0.15, 0.2, 0.25, 0.3, 0.35, 0.4, 0.45, 0.5, 0.6, 0.7, 0.8, 0.9, 1, 1.5, 2, 2.5, 3, 4, or about 5 or more gallons per minute per cubic foot of ceramic substrate.

During the denitrifying the total retention time of the deoxygenated water in the substrate including the immobilized bacteria can be sufficient to denitrify the water to suitable levels, such as about 0.1 minutes to about 720 minutes, or about 20 minutes to about 120 minutes, or about 0.1 minutes or less, or less than, equal to, or greater than about 0.5 min, 1, 2, 4, 6, 8, 10, 15, 20, 25, 50, 75, 100, 150, 200, 250, 300, 400, 500, 600, 700, 800, or about 720 minutes or more.

During the denitrifying, the flow velocity of the deoxygenated water through the substrate including the immobilized bacteria can be below about 100 ft/s, or about 0.001 ft/s to about 10 ft/s, or about 0.001 ft/s or less, or less than, equal to, or greater than about 0.005, 0.01, 0.05, 0.1, 0.5, 1, 1.5, 2, 2.5, 3, 3.5, 4, 4.5, 5, 6, 7, 8, 9, or about 10 ft/s or more.

Growing or Maintaining Bacteria on a Substrate.

In various embodiments, a method of denitrifying water using bacteria immobilized on a substrate can include growing or maintaining the immobilized bacteria on the substrate or growing the immobilized bacteria on the substrate. In various embodiments, the present invention provides a method of immobilizing or maintaining bacteria on a substrate for denitrification of water, the method including deoxygenating water including a water-soluble form of nitrogen, and exposing the deoxygenated water to denitrifying bacteria on or within a porous substrate to grow or maintain immobilized bacteria on the porous substrate, to convert the water-soluble form of nitrogen in the water to nitrogen gas that is removed, and to form a denitrified water. Growing or maintaining can be a part of any embodiment of the method of denitrifying water described herein, and can include any suitable feature described herein with respect to the denitrification method, or it can be an independent method of establishing or maintaining bacteria on the substrate that is performed without denitrification as the primary goal (although denitrification will still occur). Growing or maintaining can be performed continuously or intermittently during a method of denitrification using the bacteria.

Growing or maintaining can include exposing bacteria to the substrate, and can include providing good growth conditions for the bacteria, such food or nutrients, and such as anaerobic conditions that include dissolved forms of nitrogen to support the growth and maintenance of desired anaerobic denitrifying bacteria. In some embodiments, for the purposes of growing or maintaining the bacteria, water-soluble nitrogen can be added to the water, and water from non-natural sources can be used if desired. In other embodiments, the water used for growing or maintaining is water taken from a natural source. The water is optionally oxidized prior to exposing to the bacteria to convert at least some nitrogen to water-soluble forms, and is deoxygenated if needed to provide a sufficiently anaerobic environment for the bacteria. The water can have oxygen and nitrogen concentrations as described for embodiments of the denitrification method. The water can include nutrients or food in any suitable concentration, as described for embodiments of the denitrification method. The water can optionally be recirculated back to the substrate to facilitate growth or maintenance of the bacteria.

Growing or maintaining the bacteria on the substrate can include first inoculating the bacteria (e.g., a soil sample containing the bacteria) in an anaerobic nutritional broth before exposing (e.g., seeding) the bacteria to the substrate to grow the bacteria thereon. Growing or maintaining the bacteria can include maintaining a culture of the bacteria for growth and maintenance of the bacteria on the substrate. Growing or maintaining bacteria on the substrate can include flowing the water including the water-soluble form of nitrogen that also includes food or nutrients and the bacteria (which is optionally inoculated first) through the substrate to grow or maintain the bacteria on the substrate.

In some embodiments, growing or maintaining the bacteria on the substrate can include using a lower flow rate than used during the denitrification method; in other embodiments, the flow rates can be similar. Growing or maintaining the bacteria can include flowing the water including the water-soluble form of nitrogen past the bacteria immobilized on the substrate at a suitable flow rate, such as a flow rate of about 0.001 gallons per minute per cubic foot of ceramic substrate to about 5 gallons per minute per cubic foot of ceramic substrate, or about 0.001 to about 1, 2, or 3 gallons per minute per cubic foot of ceramic substrate, or about 0.001 or less, or less than, equal to, or greater than about 0.005, 0.01, 0.05, 0.1, 0.15, 0.2, 0.25, 0.3, 0.35, 0.4, 0.45, 0.5, 0.6, 0.7, 0.8, 0.9, 1, 2, 3, 4, or about 5 or more gallons per minute per cubic foot of ceramic substrate. Water including the water-soluble form of nitrogen, food and nutrient broth, and the bacteria can be flowed through the substrate at a velocity of about 0.001 ft/s to 100 ft/s, or about 0.001 ft/s to 1 ft/s, or about 0.001 ft/s or less, or less than, equal to, or greater than about 0.005, 0.01, 0.05, 0.1, 0.5, 1, 1.5, 2, 2.5, 3, 4, 5, 6, 8, 10, 12, 14, 16, 18, 20, 25, 30, 40, 50, 60, 70, 80, 90, or about 100 ft/s or more.

Exposing the bacteria to the substrate to grow or maintain bacteria on the substrate can include flowing water including the water-soluble form of nitrogen and the food and nutrient broth include about 0.1 gallons to about 10 gallons of a bacterial concentrate, or about 1 gallon, or less than about 0.1, or less than, equal to, or greater than about 0.2, 0.4, 0.6, 0.8, 1, 1.5, 2, 2.5, 3, 3.5, 4, 4.5, 5, 6, 7, 8, 9, or about 10 gallons or more of a bacterial concentrate including the bacteria per 100 gallons of the water and the broth, wherein the bacterial concentration having a concentration of about $10^5$ colony forming units per ml (CFU/ml) to $10^{16}$ CFU/ml of denitrifying bacteria, or about $10^8$ colony forming units per ml (CFU/ml) to $10^{13}$ CFU/ml of denitrifying bacteria, or about $10^5$ or less, or less than, equal to, or greater than about $10^6$, $10^7$, $10^8$, $10^9$, $10^{10}$, $10^{11}$, $10^{12}$, $10^{13}$, $10^{14}$, $10^{15}$, or about $10^{16}$ or more CFU/ml of denitrifying bacteria.

Denitrifying Bacterial Substrate.

Various embodiments of the present invention provide a denitrifying bacterial substrate, such as any substrate including immobilized denitrifying bacteria described herein for use in embodiments of the method of denitrification or that can be formed using an embodiment of the method of growing or maintaining the bacteria on a substrate. For example, in various embodiments, the present invention provides a denitrifying bacterial substrate that includes a porous substrate. The denitrifying bacterial substrate also includes an immobilized bacteria on the substrate. The bacteria on the substrate can be cultured from or identical to anaerobic denitrifying bacteria in the local native environment. In some embodiments, the immobilized bacteria include *Pseudomonas stutzeri, Pseudomonas denitrificans, Pseudomonas aeruginosa*, or a combination thereof.

EXAMPLES

Various embodiments of the present invention can be better understood by reference to the following Examples which are offered by way of illustration. The present invention is not limited to the Examples given herein.

Equipment and materials used in the Examples included those shown in Table 1.

TABLE 1

Equipment and materials.

| Equipment/material | Manufacturer (if available) | Model/Lot # (if available) |
|---|---|---|
| 20 L carboys | Nalgene | |
| Ferric chloride | Brenntag | Lot #: 345039527061 |
| Sodium metabisulfite | Calabrian | Lot #: 40C7 |
| Sucrose (table sugar) | | |
| Ammonium calcium nitrate fertilizer. 14.5% Nitrate nitrogen, 1% ammonical nitrogen, 19% calcium. | Greenway Biotech, Inc. | |
| Sodium hypochlorite | Brenntag | Lot #: 586604528088 |
| Yeast extract | Biobasic Canada, Inc. | Lot #: K631EXL0 |
| Potassium nitrate | | Lot #:50005861 |
| Sodium chloride (table salt) | | |
| Peristaltic pumps | Cole Parmer | MasterFlex L/S |
| Spectrophotometer | HACH | DR6000 |
| Dissolved oxygen probe | HACH | LDO |
| pH meter | Oakton ® | p150 |
| DPD total chlorine reagent | HACH | Lot #: A8092 |
| Iron reagent | HACH | 1 FerroVer ®/ Lot #: A7153 |
| Hemocytometer | LW Scientific | |
| Microscope | Omax | |
| Tubing (withstands 0.25 GPM) | MasterFlex | |
| Tubing (withstands 2 to 20 ml/min) | MasterFlex | |
| PVC pipping (withstands 0.25 GPM) | Spears | |
| Static mixer | | |
| 250-gallon totes | | |
| Ion chromatography system | Thermo Scientific ™ | Dionex Aquion |
| Deoxygenation column (5.76 in ID, 42 in long) | Spears | |
| Denitrification column (7.625 in ID, 84 in long) | Spears | |
| Ceramic substrate | | As described below. |
| Incubator | Digisystem Laboratory Instruments | |
| Nitrogen gas-airgas company | | |

Ceramic substrate. A mortar-style mixer was used, although another suitable mixing device could be used such as a paddle or ribbon blender. In the mortar mixer, 250 lbs (113 kg) of red clay having the composition described in Table 2 and having about a 5 wt % moisture content, was mixed with 25 lbs (11.3 kg) of Canadian peat, (optionally, not performed in this Example, this can be substituted or supplemented by sawdust or other combustible organic material with an ash content of less than 10 wt %), and 5 lbs (2.3 kg) of quicklime with a CaO content of 94 wt % or greater. The total CaO content was about 2 wt %. These materials were mixed in their native state for approximately 5 minutes after which 70 lbs (31.8 kg) of water was slowly added to form a uniformly moist mixture. This moist mixture was mixed for an additional 5 minutes and then was removed from the mixer. Upon removal of the mixture, it was fed uniformly through an extrusion device to produce a pellet. The extrusion die was considered a shearing plate die so as to avoid unnecessary compression of the pellet which could reduce its ultimate porosity. Optionally, not performed in this Example, for enhanced pellet compression, extrusion can be performed under vacuum to remove entrained air. Following the extrusion process, the resulting pellets were placed in a kiln where they were heated to a final temperature of approximately 1950° F. The final pellets had a diameter of 0.25" to 0.38" (0.64 cm to 0.95 cm) and a length of 0.25" to 1" (0.64 cm to 2.54 cm).

TABLE 2

Red clay analysis.

| MATERIAL | DRY WEIGHT % | FIRED WEIGHT % |
|---|---|---|
| Loss on ignition (1050 °C.) | 6.5 | |
| Silica ($SiO_2$) | 59.6 | 63.7 |
| Alumina ($Al_2O_3$) | 17.7 | 18.9 |
| Iron Oxide ($Fe_2O_3$) | 8.6 | 9.2 |
| Titanium Oxide ($TiO_2$) | 1.0 | 1.1 |
| Calcium Oxide (CaO) | 0.78 | 0.81 |
| Magnesium Oxide (MgO) | 1.9 | 2.0 |
| Potassium Oxide ($K_2O$) | 3.2 | 3.5 |
| Sodium Oxide ($Na_2O$) | 0.65 | 0.70 |
| Manganese Oxide (MnO) | 0.11 | 0.12 |
| Phosphate ($P_2O_5$) | <0.25 | <0.25 |

Example 1. Bacterial Isolation

Soil samples of 5-10 grams were added to 200 ml of deionized (DI) water, with 10 grams of sodium chloride, 1 g of yeast extract, and 20 ppm of potassium nitrate. Nitrogen gas was bubbled through the solution until the dissolved oxygen content was below 0.2 ppm, to form an anaerobic solution.

The anaerobic solution was stored at 40° C. in an incubator for 72 hours. Due to this extreme environment, the survival of bacteria in the sample was very selective. Anaerobic denitrifying species of the soil sample grew in the nutritional broth, saturating the solution with the denitrifying species. Other species may be present in the solution in minor concentrations; however, the sample was considered isolated with denitrifying bacteria because denitrifying bacteria was the only viable species under the conditions used.

Using a hemocytometer and a microscope, the initial cell counts of denitrifying bacteria started at approximately 1,000,000 cells/ml and saturated to 53,000,000 cells/ml after incubating for 72 hours. The total cell count was assumed to be substantially all (e.g., 100%) denitrifying bacteria after the incubation, due to the lack of oxygen.

Example 2. Bacterial Seeding

The bacteria were seeded and established in a ceramic media column. The column was an 8-inch diameter (7.625-inch ID) by 84-inch long column, containing a ceramic media substrate. Using the concentrated broth formed in Example 1, the column was seeded by introducing 250 mL of the broth via syringe into tubing leading into the column at about 1 L/min two times a day for three days, injecting a total of about 1.5 L of broth, after which additions were ceased and the column was allowed to populate on its own. The broth was dosed inline directly prior to the media column and followed the 0.25 GPM flow of the system. Bacteria naturally adhered to the porous substrate when introduced therein. Water flowing into the column contained nutrients including sucrose and dissolved nitrogen, and had the same composition as the deoxygenated "influent water" described in Example 3.

Visual colony formation was an indicator of increasing cell populations and proper nutrient dosing. A similar column was prepared with DI water and media for color comparison, which roughly indicated the degree of bacterial growth. Bacterial counts of the effluent and influent water were conducted daily. As bacterial cell counts dropped from approximately 2,000,000 cells/mL to 100,000 cells/mL in the effluent, more colonies were observed inside the substrate, along with increasing nitrate removal from the water. Less bacteria counted in the effluent indicated improving bacterial affinity for the ceramic substrate. The column was fully seeded and ready for denitrification after about 1 to 3 weeks.

Example 3. Denitrification of Water

Environmental water from a retention pond (location: 28° 02'00.2"N 82° 02'46.1"W 28.033375, −82.046148) was stored in three 250-gallon totes, to allow for continuous flow. The soil sample used in Example 1 to isolate the bacteria was taken from the soil within the pond itself, from the pond's soil bed approximately 1 foot from the pond's water line and 6 inches below the surface of the ground. The stored water was dosed with 9.34-18.68 ppm ammonium calcium nitrate fertilizer. The environmental water was spiked with additional nitrates to demonstrate that the method can be used to reduce higher concentrations of nitrogen. The amount added was sufficient to bring the nitrate concentration in the environmental water to about 3 to 10 ppm.

Figure 1:
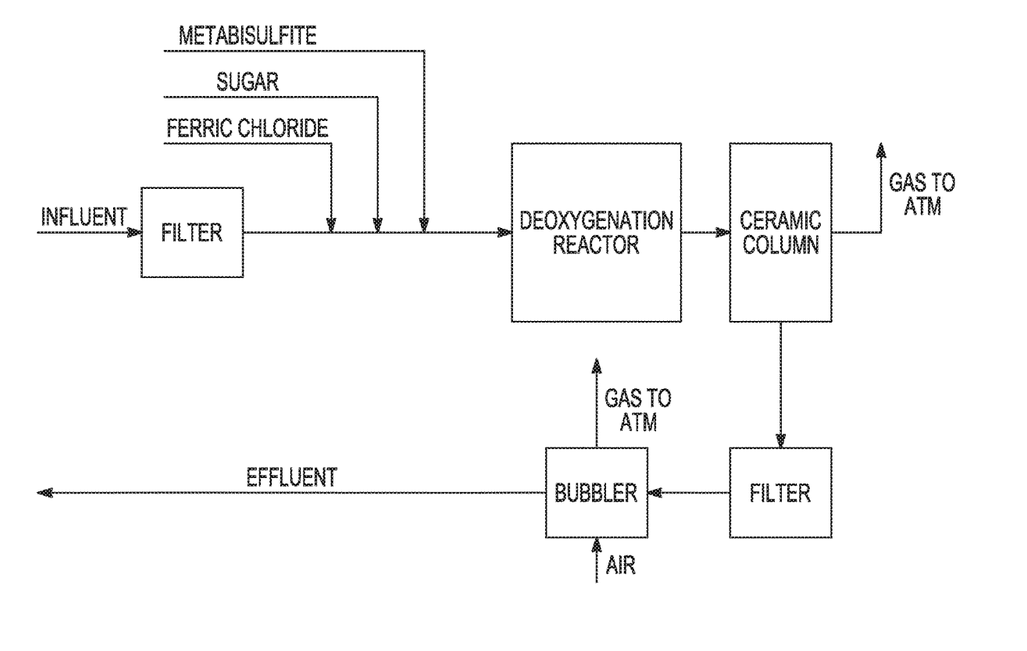
FIG. 1 illustrates a denitrification process, in accordance with various embodiments.

Referring to FIG. 1, illustrating the denitrification process, the environmental water having 3 to 10 ppm concentration of nitrate, referred to as "influent water," was pumped from the storage totes at 0.25 GPM.

The deoxygenation and pretreatment chemicals were stored in two 20 L Nalgene carboys combining nonreactive chemicals to minimize equipment needs. To the influent water, 0.2 g/L ferric chloride was dosed at a rate of 4.1 mL/min to increase the total iron concentration by 0.3 ppm yielding a total iron concentration of approximately 0.8 ppm after treatment. Next, solutions of 66 g/L sucrose and 40 g/L sodium metabisulfite (formed using DI water) were dosed to the influent water at a rate of 4.7 mL/min to bring the sucrose and sodium metabisulfite concentrations up to approximately 100 ppm and 200 ppm, respectively.

The influent water with ferric chloride, sucrose, and sodium meta bisulfite was then fed through a static mixer and into the deoxygenation column (i.e., deoxygenation reactor). The deoxygenation column was a 6-inch diameter (5.76 in ID) by 42-inch long, clear, PVC column. An average residence time of approximately 19 minutes was used to allow the sodium metabisulfite and iron catalyst to deoxygenate the water. Upon exiting the column, the water had a dissolved oxygen content of 0.0-0.3 ppm.

Following the oxygen removal column, the water was flowed by gravity into the bottom of the bacterial media column formed in Example 2. The bacterial media column had a total void space within the column of approximately 69%, and an average residence time of approximately 46 minutes was used. As the process water flowed through the bacteria column, the bacteria anaerobically extracted and consumed the oxygen contained in the nitrogen species present in the water, systematically reducing nitrate to nitrite, nitrite to nitric oxide, nitric oxide to nitrous oxide, and finally nitrous oxide to nitrogen gas. After 46 minutes in the column, about 90%-100% of nitrates were removed, or approximately 3-10 ppm nitrate were removed, depending on the influent concentration. The nitrogen gas produced by the bacteria bubbled through the column, which may aid in maintaining a low dissolved oxygen concentration. In addition, the nitrogen gas produced added a small amount of positive pressure which helped keep atmospheric oxygen out of the column and associated tubing, helping to prevent reoxygenation.

After the 46-minute hold time in the column, the treated water and nitrogenous gases then left through the top of the column through an overflow line and were released back into the environment after ensuring that the effluent met all surface water quality standards.

Samples were taken from sample points located at the environmental water storage totes, between the deoxygenation column and the bacteria substrate column, and at the effluent of the bacteria substrate column. Nitrate, nitrite, chloride, and sulfate levels were evaluated using ion chromatography. Water quality was measured by testing for iron and free chlorine levels in the effluent by utilizing colorimetric methods and spectrophotometry.

Table 3 illustrates nitrate, nitrite, sulfate, and chloride concentrations before and after the denitrification. All the data outlined is from ion chromatography (IC) analysis, in which some samples were preserved with acid, which can add ions to the solution like chloride (e.g., via HCl preservation). For each fertilizer concentration, two days of back-to-back data is shown with the three daily sample points and the water analysis of ions.

TABLE 3

Nitrate, nitrite, sulfate, and chloride concentrations the before and after denitrification.

| Sample Identification | Nitrate mg/L | Nitrite mg/L | Sulfate mg/L | Chloride mg/L |
|---|---|---|---|---|
| Jun. 14, 2018 | 9.34 mg/L Fertilizer preserved with HCl (pH <2) | | | |
| Pre-column 9:00 AM | 3.2724 | .0652 | 218.3803 | 615.1783 |
| Effluent 9:00 AM | 0 | 0 | 176.7587 | 435.7865 |
| Pre-column 12:00 PM | 5.2842 | 0 | 338.3078 | 631.7204 |
| Effluent 12:00 PM | 0 | 0 | 195.3256 | 630.0836 |
| Pre-column 3:00 PM | 4.7412 | 0 | 332.5783 | 471.3092 |
| Effluent 3:00 PM | 0 | 0 | 178.3986 | 518.5549 |
| Jun. 15, 2018 | 9.34 mg/L Fertilizer; preserved with HCl (pH <2) | | | |
| Pre-column 9:00 AM | 3.2537 | 0 | 470.061 | 914.1378 |
| Effluent 9:00 AM | 0 | 0 | 246.1402 | 933.3716 |
| Pre-column 12:00 PM | 3.6826 | 0 | 330.969 | 939.5036 |
| Effluent 12:00 PM | 0 | 0 | 247.7452 | 921.9721 |
| Pre-column 3:00 PM | 3.9022 | 0 | 290.5353 | 1014.7161 |
| Effluent 3:00 PM | 0 | 0 | 286.2901 | 1159.8046 |
| Jun. 21, 2018 | 18.68 mg/L Fertilizer | | | |
| Pre-column 9:00 AM | 5.9739 | .050 | 235.5634 | 40.9524 |
| Effluent 9:00 AM | 0 | 0 | 165.1446 | 31.5865 |
| Pre-column 12:00 PM | 9.0532 | 0 | 220.1237 | 33.4551 |
| Effluent 12:00 PM | .3559 | 0 | 392.9978 | 34.5139 |
| Pre-column 3:00 PM | 9.1077 | 0 | 231.9326 | 32.7178 |
| Effluent 3:00 PM | .7382 | C | 180.2002 | 33.1777 |
| Jun. 22, 2018 | 18.68 mg/L Fertilizer | | | |
| Pre-column 9:00 AM | 8.1775 | 0 | 167.4173 | 34.086 |
| Effluent 9:00 AM | 0 | 0 | 211.3472 | 33.4849 |
| Pre-column 12:00 PM | 8.9524 | .2123 | 173.7937 | 33.1163 |
| Effluent 12:00 PM | 0 | 0 | 169.466 | 33.2099 |
| Pre-column 3:00 PM | 7.6133 | .8775 | 127.1137 | 32.4791 |
| Effluent 3:00 PM | 0 | 0 | 135.7094 | 32.8589 |

Table 4 illustrates NO$_3$/NO$_2$ concentration, total Kjeldahl nitrogen (TKN), and total nitrogen before and after the denitrification. The data was provided by PhosLab Environmental Services, Inc., with nitrate/nitrite colorimetry by method EPA 353.2 and TKN colorimetry by method EPA 351.2 used for the analysis of Nitrogen species. PhosLab testing methods followed National Environmental Accreditation Program (NELAP) standards. Total nitrogen calculated with the sum of NO$_3$/NO$_2$ and TKN mg/L of less than 0.02 mg/L indicated that the nitrate and nitrite concentrations were under the detection range of about 20 ppb. For total nitrogen additions, the nitrate was assumed at the highest concentration of 20 ppb for calculations.

TABLE 4

NO$_3$/NO$_2$ Concentration, total Kjeldahl nitrogen (TKN), and total nitrogen before and after denitrification.

| Sample | NO$_3$/NO$_2$-N mg/L | TKN-N mg/L | Total nitrogen mg/L |
|---|---|---|---|
| May 31, 2018 | 9.34 mg/L Fertilizer; preserved with sulfuric acid (pH <2) | | |
| Influent 9:00 AM | .686 | .749 | 1.435 |
| Effluent 9:00 AM | <.02 | 1.22 | 1.24 |
| Jun. 4, 2018 | 9.34 mg/L Fertilizer; preserved with sulfuric acid (pH <2) | | |
| Influent 12:00 PM | .966 | .549 | 1.515 |
| Effluent 12:00 PM | <.02 | .898 | .918 |
| Jun. 5, 2018 | 9.34 mg/L Fertilizer; preserved with sulfuric acid (pH <2) | | |
| Influent 9:00 AM | .927 | .612 | 1.539 |
| Effluent 9:00 AM | <.02 | .584 | .604 |

Example 4. Oxidation and Deoxygenation

Example 3 was repeated, but an oxidation was performed as a pre-treatment stage. Sodium hypochlorite was added at a concentration of about 15 ppm and was allowed to mix for 5 to 20 minutes before the addition of meta-bisulfite at a concentration of about 100 ppm for deoxygenation. The time required for deoxygenation decreased from 90 to 20 minutes or less and the amount of sodium meta-bisulfite required was reduced by 50 wt %. The dissolved oxygen level was continuously measured, and reached 0.2 ppm dissolved oxygen after 5-20 minutes.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

EXEMPLARY EMBODIMENTS

The following exemplary embodiments are provided, the numbering of which is not to be construed as designating levels of importance:

Embodiment 1 provides a method of denitrification of water, the method comprising:
deoxygenating water comprising a water-soluble form of nitrogen;
exposing the deoxygenated water to denitrifying bacteria to convert the water-soluble form of nitrogen in the water to nitrogen gas that is removed and to form a denitrified water; and
reoxygenating the denitrified water.

Embodiment 2 provides the method of Embodiment 1, wherein the water comprising the water-soluble form of nitrogen has a nitrogen concentration of about 0.1 ppm to about 10 ppm total nitrogen.

Embodiment 3 provides the method of any one of Embodiments 1-2, wherein the water comprising the water-soluble form of nitrogen has a nitrogen concentration of about 1 ppm to about 4 ppm total nitrogen.

Embodiment 4 provides the method of any one of Embodiments 1-3, wherein the water comprising the water-soluble form of nitrogen has a nitrate concentration of about 0.01 ppm to about 10 ppm.

Embodiment 5 provides the method of any one of Embodiments 1-4, wherein the water comprising a water-soluble form of nitrogen has a nitrate concentration of about 1 ppm to about 3 ppm.

Embodiment 6 provides the method of any one of Embodiments 1-5, wherein the denitrified, reoxygenated water has a nitrogen concentration of about 0.0 ppm to about 2 ppm total nitrogen.

Embodiment 7 provides the method of any one of Embodiments 1-6, wherein the denitrified, reoxygenated water has a nitrogen concentration of about 0.5 ppm to about 0.8 ppm total nitrogen.

Embodiment 8 provides the method of any one of Embodiments 1-7, wherein the denitrified, reoxygenated water has a total nitrogen concentration that is about 0% to about 70% of the total nitrogen concentration of the water comprising the water-soluble form of nitrogen.

Embodiment 9 provides the method of any one of Embodiments 1-8, wherein the denitrified, reoxygenated water has a total nitrogen concentration that is about 20% to about 60% of the total nitrogen concentration of the water comprising the water-soluble form of nitrogen.

Embodiment 10 provides the method of any one of Embodiments 1-9, wherein the denitrified, reoxygenated water has a nitrate concentration that is about 0.0 ppm to about 2 ppm.

Embodiment 11 provides the method of any one of Embodiments 1-10, wherein the denitrified, reoxygenated water has a nitrate concentration that is about 0.0 ppm to about 0.8 ppm.

Embodiment 12 provides the method of any one of Embodiments 1-11, wherein the denitrified, reoxygenated water has a nitrate concentration that is about 0% to about 70% of the nitrate concentration of the water comprising the water-soluble form of nitrogen.

Embodiment 13 provides the method of any one of Embodiments 1-12, wherein the denitrified, reoxygenated water has a nitrate concentration that is about 0% to about 60% of the nitrate concentration of the water comprising the water-soluble form of nitrogen.

Embodiment 14 provides the method of any one of Embodiments 1-13, wherein the method is a continuous process.

Embodiment 15 provides the method of any one of Embodiments 1-14, wherein the water comprising the water-soluble form of nitrogen further comprises nitrogen that is in a water-insoluble form.

Embodiment 16 provides the method of any one of Embodiments 1-15, wherein the water-soluble form of nitrogen in the water comprises nitrate ($NO_3^-$), nitrite ($NO_2^-$), nitric oxide (NO), nitrous oxide ($N_2O$), nitrogen gas ($N_2$), or a combination thereof.

Embodiment 17 provides the method of any one of Embodiments 1-16, wherein the water-soluble form of nitrogen in the water is nitrate ($NO_3^-$).

Embodiment 18 provides the method of any one of Embodiments 1-17, further comprising oxidizing or hydrolytically converting nitrogen in water comprising the nitrogen to form the water comprising the water-soluble form of nitrogen.

Embodiment 19 provides the method of any one of Embodiments 1-18, wherein the oxidation or hydrolysis comprises treatment with acid, base, ferrate, ozone, ferric chloride, potassium permanganate, potassium dichromate, potassium chlorate, potassium persulfate, sodium persulfate, perchloric acid, peracetic acid, potassium monopersulfate, hydrogen peroxide, sodium hypochlorite, potassium hypochlorite, or a combination thereof.

Embodiment 20 provides the method of any one of Embodiments 1-19, wherein the water comprising the water-soluble form of nitrogen has an oxygen concentration of about 0 ppm to about 20 ppm oxygen.

Embodiment 21 provides the method of any one of Embodiments 1-20, wherein the water comprising the water-soluble form of nitrogen has an oxygen concentration of about 2 ppm to about 8 ppm.

Embodiment 22 provides the method of any one of Embodiments 1-21, wherein the deoxygenated water has an oxygen concentration of about 0 ppm to about 2 ppm.

Embodiment 23 provides the method of any one of Embodiments 1-22, wherein the deoxygenated water has an oxygen concentration of about 0 ppm to about 0.3 ppm.

Embodiment 24 provides the method of any one of Embodiments 1-23, wherein the deoxygenating comprises treating with one or more deoxygenating compounds, sulfite compounds, catalysts, heating, exposing to reduced pressure, sparging with a stripping gas, sonicating, contacting with a membrane contactor, or a combination thereof.

Embodiment 25 provides the method of any one of Embodiments 1-24, wherein the deoxygenating comprises exposing the water comprising the water-soluble form of nitrogen to one or more sulfite compounds in the presence of a metal catalyst.

Embodiment 26 provides the method of any one of Embodiments 1-25, wherein the deoxygenating is performed for about 1 second to about 1 day.

Embodiment 27 provides the method of any one of Embodiments 1-26, wherein the deoxygenating is performed for about 1 minute to about 30 minutes.

Embodiment 28 provides the method of any one of Embodiments 25-27, wherein the one or more sulfite compounds comprise sodium sulfite, potassium sulfite, sodium bisulfite, sodium metabifsulfite, potassium bisulfite, potassium metabisulfite, or a combination thereof.

Embodiment 29 provides the method of any one of Embodiments 25-28, wherein the metal catalyst comprises iron, copper, cobalt, a platinum group metal, or a combination thereof.

Embodiment 30 provides the method of any one of Embodiments 25-29, wherein the metal catalyst comprises an iron catalyst.

Embodiment 31 provides the method of any one of Embodiments 25-30, wherein the metal catalyst is a homogeneous catalyst or a heterogeneous catalyst.

Embodiment 32 provides the method of any one of Embodiments 25-31, wherein a concentration of the metal catalyst is about 10 ppb to about 10,000 ppb.

Embodiment 33 provides the method of any one of Embodiments 25-32, wherein a concentration of the metal catalyst is about 400 ppb to about 1,000 ppb.

Embodiment 34 provides the method of any one of Embodiments 25-33, wherein each liter of the deoxygenated water is exposed to about 0.1 mg to about 100 mg of the metal catalyst in combination with the one or more sulfites.

Embodiment 35 provides the method of any one of Embodiments 25-34, wherein the one or more sulfite compounds are used in a concentration of about 10 ppb to about 10,000 ppb.

Embodiment 36 provides the method of any one of Embodiments 25-35, wherein the one or more sulfite compounds are used in a concentration of about 100 ppb to about 250 ppb.

Embodiment 37 provides the method of any one of Embodiments 25-36, wherein the one or more sulfites are added in an amount of about 1 ppm to about 10,000 ppm per 1 ppm dissolved oxygen.

Embodiment 38 provides the method of any one of Embodiments 25-37, wherein the one or more sulfites are added in an amount of about 5 ppm to about 25 ppm per 1 ppm dissolved oxygen.

Embodiment 39 provides the method of any one of Embodiments 1-38, comprising filtering the water prior to performing the deoxygenating.

Embodiment 40 provides the method of any one of Embodiments 1-39, adding nutrients, food, or a combination thereof, to the water.

Embodiment 41 provides the method of Embodiment 40, wherein the nutrients or food are added prior to the denitrification, during the denitrification, or a combination thereof.

Embodiment 42 provides the method of any one of Embodiments 40-41, wherein the nutrients or food are added prior to the deoxygenating, during the deoxygenating, after the deoxygenating, or a combination thereof.

Embodiment 43 provides the method of any one of Embodiments 40-42, wherein the nutrients comprise compounds comprising nitrogen, sulfur, phosphorus, potassium, iron, molybdenum, tungsten, magnesium, calcium, sodium, copper, or a combination thereof.

Embodiment 44 provides the method of any one of Embodiments 40-43, wherein the nutrients comprise iron chloride.

Embodiment 45 provides the method of any one of Embodiments 40-44, wherein the food and nutrients are added to maintain a concentration of molybdenum in the deoxygenated water fed to the denitrifying bacteria of 0.01 ppb to about 100 ppb.

Embodiment 46 provides the method of any one of Embodiments 40-45, wherein the food and nutrients are added to maintain a concentration of molybdenum in the deoxygenated water fed to the denitrifying bacteria of about 0.1 ppb to about 20 ppb.

Embodiment 47 provides the method of any one of Embodiments 40-46, wherein the food and nutrients are added to maintain a concentration of the combination of iron and copper in the deoxygenated water fed to the denitrifying bacteria of about 50 ppb to about 10,000 ppb.

Embodiment 48 provides the method of any one of Embodiments 40-47, wherein the food and nutrients are added to maintain a concentration of the combination of iron and copper in the deoxygenated water fed to the denitrifying bacteria of about 200 ppb to about 2,000 ppb.

Embodiment 49 provides the method of any one of Embodiments 40-48, wherein the food and nutrients are added to maintain a concentration of iron in the deoxygenated water fed to the denitrifying bacteria of about 25 ppb to about 5,000 ppb.

Embodiment 50 provides the method of any one of Embodiments 40-49, wherein the food and nutrients are added to maintain a concentration of iron in the deoxygenated water fed to the denitrifying bacteria of about 100 ppb to about 1,000 ppb.

Embodiment 51 provides the method of any one of Embodiments 40-50, wherein the food and nutrients are added to maintain a concentration of copper in the deoxygenated water fed to the denitrifying bacteria of about 25 ppb to about 5,000 ppb.

Embodiment 52 provides the method of any one of Embodiments 40-51, wherein the food and nutrients are added to maintain a concentration of copper in the deoxygenated water fed to the denitrifying bacteria of about 100 ppb to about 1,000 ppb.

Embodiment 53 provides the method of any one of Embodiments 40-52, wherein the food comprises a carbon source, a plant product, a bacterial product, a fungal product, an animal product, or a combination thereof.

Embodiment 54 provides the method of Embodiment 53, wherein the carbon source comprises sucrose, citric acid, cellulose fibers, wood chips, saw dust, or a combination thereof.

Embodiment 55 provides the method of any one of Embodiments 40-54, wherein the food comprises sucrose, fructose, glucose, acetic acid, carbon dioxide, citrate, yeast extract, or a combination thereof.

Embodiment 56 provides the method of any one of Embodiments 40-55, wherein the food comprises sucrose.

Embodiment 57 provides the method of any one of Embodiments 40-56, wherein the nutrients and food are added in an amount such that the carbon to nitrate ratio is between about 0.01 mg carbon per 1 mg nitrate to about 1 g carbon per 1 mg nitrate.

Embodiment 58 provides the method of any one of Embodiments 40-57, wherein the nutrients and food are added in an amount such that the carbon to nitrate ratio is between about 1 mg carbon per 1 mg nitrate to about 5 mg carbon per 1 mg nitrate.

Embodiment 59 provides the method of any one of Embodiments 40-58, comprising filtering the deoxygenated water prior to adding nutrients or food thereto.

Embodiment 60 provides the method of any one of Embodiments 1-59, wherein the denitrifying bacteria is in solution, immobilized, or a combination thereof.

Embodiment 61 provides the method of any one of Embodiments 1-60, wherein the denitrifying bacteria is an immobilized denitrifying bacteria.

Embodiment 62 provides the method of any one of Embodiments 1-61, wherein the denitrifying bacteria is immobilized in or on an inorganic material, a natural polymer, a synthetic polymer, a porous substrate, an aerogel, a matrix, fibers, or a combination thereof.

Embodiment 63 provides the method of any one of Embodiments 1-62, wherein the denitrifying bacteria is immobilized on a porous substrate.

Embodiment 64 provides the method of Embodiment 63, wherein the porous substrate comprises a synthetic substrate, a natural substrate, a ceramic, a metal, a clay, a polymer, a natural mineral, rock, activated carbon, zeolite, cement, a ceramic foam, diatomaceous earth, silica, glass, charcoal, or a combination thereof.

Embodiment 65 provides the method of any one of Embodiments 63-64, wherein the porous substrate comprises a ceramic and a reactive calcium available to form a solid calcium salt with an anionic material.

Embodiment 66 provides the method of any one of Embodiments 63-65, wherein the porous substrate is a vitrified mixture of a non-clumping clay, dolomitic limestone, CaO, and peat.

Embodiment 67 provides the method of Embodiment 66, wherein
about 50 wt % to about 80 wt % of the vitrified mixture is the non-clumping clay,
about 5 wt % to about 20 wt % of the vitrified mixture is dolomitic limestone, such that about 0.1 wt % to about 5 wt % of the vitrified mixture is magnesium,
about 0.1 wt % to about 10 wt % of the vitrified mixture is $CaCO_3$,
about 0.01 wt % to about 5 wt % of the vitrified mixture is CaO,
about 1 wt % to about 20 wt % of the vitrified mixture is peat,
about 0 wt % to about 30 wt % of the vitrified mixture is water.

Embodiment 68 provides the method of any one of Embodiments 1-67, wherein the denitrifying bacteria is indigenous to soil in the natural location of the water containing the water-soluble form of nitrogen.

Embodiment 69 provides the method of any one of Embodiments 1-68, wherein the denitrifying bacteria is cultured from bacteria taken from soil in the natural location of the water containing the water-soluble form of nitrogen.

Embodiment 70 provides the method of any one of Embodiments 1-69, wherein the denitrifying bacteria comprises *Thiobacillus denitrificans*, *Micrococcus denitrificans*, a *Serratia*, a *Pseudomonas*, an *Achromobacter*, a alkaligenes, a *bacillus*, or a combination thereof.

Embodiment 71 provides the method of any one of Embodiments 1-70, wherein the denitrifying bacteria comprises a *Pseudomonas*.

Embodiment 72 provides the method of any one of Embodiments 1-71, wherein the denitrifying bacteria is chosen from *Pseudomonas stutzeri, Pseudomonas denitrificans, Pseudomonas aeruginosa*, and combinations thereof.

Embodiment 73 provides the method of any one of Embodiments 1-72, wherein the denitrifying bacteria transform nitrate in the deoxygenated water into nitrogen gas.

Embodiment 74 provides the method of any one of Embodiments 1-73, wherein the denitrifying bacteria reduces nitrate ($NO_3^-$) to nitrite ($NO_2^-$), reduces nitrite ($NO_2^-$) to nitric oxide (NO), reduces nitric oxide (NO) to nitrous oxide ($N_2O$), reduces nitrous oxide ($N_2O$) to nitrogen gas ($N_2$), or a combination thereof.

Embodiment 75 provides the method of any one of Embodiments 1-74, wherein formation of hydrogen sulfide is reduced or minimized by removing the water from the denitrifying bacteria once the water-soluble form of nitrogen is substantially completely transformed into nitrogen gas.

Embodiment 76 provides the method of any one of Embodiments 63-75, further comprising maintaining the immobilized bacteria on the substrate or growing the immobilized bacteria on the substrate.

Embodiment 77 provides the method of Embodiment 76, comprising inoculating the bacteria in an anaerobic nutritional broth before exposing the bacteria to the substrate to grow the bacteria thereon.

Embodiment 78 provides the method of any one of Embodiments 76-77, comprising flowing the water comprising the water-soluble form of nitrogen, food and nutrient broth, and the bacteria through the substrate to grow the bacteria on the substrate.

Embodiment 79 provides the method of any one of Embodiments 76-78, wherein during the growing or maintaining the deoxygenated water is flowed through the past the denitrifying bacteria immobilized on the porous substrate at a flow rate of about 0.001 gallons per minute per cubic foot of ceramic substrate to about 5 gallons per minute per cubic foot of ceramic substrate.

Embodiment 80 provides the method of any one of Embodiments 76-79, wherein the water comprising the water-soluble form of nitrogen, food and nutrient broth, and the bacteria is flowed through the substrate at a velocity of about 0.001 ft's to about 100 ft/s.

Embodiment 81 provides the method of any one of Embodiments 76-80, wherein the water comprising the water-soluble form of nitrogen, food and nutrient broth, and the bacteria is flowed through the substrate at a velocity of about 0.001 ft/s to about 1 ft/s.

Embodiment 82 provides the method of any one of Embodiments 76-81, wherein the water comprising the water-soluble form of nitrogen and the food and nutrient broth comprise about 0.1 gallons to about 10 gallons of a bacterial concentrate comprising the bacteria per 100 gallons of the water and the broth, the bacterial concentration having a concentration of about $10^5$ colony forming units per ml (CFU/ml) to about $10^{16}$ CFU/ml of denitrifying bacteria.

Embodiment 83 provides the method of any one of Embodiments 76-82, wherein the water comprising the water-soluble form of nitrogen and the food and nutrient broth comprise about 1 gallon of a bacterial concentrate comprising the bacteria per 100 gallons of the water and the broth, the bacterial concentration having a concentration of about $10^8$ colony forming units per ml (CFU/ml) to about $10^{13}$ CFU/ml of denitrifying bacteria.

Embodiment 84 provides the method of any one of Embodiments 1-83, comprising culturing the bacteria on a medium to verify desired species, anaerobic, population, growth rate, or a combination thereof.

Embodiment 85 provides the method of any one of Embodiments 63-84, wherein during the denitrifying the deoxygenated water is flowed through the past the denitrifying bacteria immobilized on the porous substrate at a flow rate of 0.001 gallons per minute per cubic foot of ceramic substrate to 5 gallons per minute per cubic foot of ceramic substrate.

Embodiment 86 provides the method of any one of Embodiments 63-85, wherein during the denitrifying the deoxygenated water is flowed through the past the denitrifying bacteria immobilized on the porous substrate at a flow rate of 0.04 gallons per minute per cubic foot of ceramic substrate to 0.26 gallons per minute per cubic foot of ceramic substrate.

Embodiment 87 provides the method of any one of Embodiments 63-86, wherein during the denitrifying the total retention time of the deoxygenated water in the substrate comprising the immobilized bacteria is about 0.1 minutes to about 720 minutes.

Embodiment 88 provides the method of any one of Embodiments 63-87, wherein during the denitrifying the total retention time of the deoxygenated water in the substrate comprising the immobilized bacteria is about 20 minutes to about 120 minutes.

Embodiment 89 provides the method of any one of Embodiments 63-88, wherein the flow velocity of the deoxygenated water through the substrate comprising the immobilized bacteria is below about 100 ft/s.

Embodiment 90 provides the method of any one of Embodiments 63-89, wherein the flow velocity of the deoxygenated water through the substrate comprising the immobilized bacteria is about 0.001 ft/s to about 10 ft/s.

Embodiment 91 provides the method of any one of Embodiments 1-90, further comprising maintaining a culture of the bacteria.

Embodiment 92 provides the method of any one of Embodiments 63-91, further comprising maintaining a culture of the bacteria for maintenance and growth of the bacteria on the substrate.

Embodiment 93 provides the method of any one of Embodiments 1-92, further comprising recirculating the denitrified water back into the process before or after the reoxygenation.

Embodiment 94 provides the method of any one of Embodiments 1-93, further comprising filtering the denitrified water.

Embodiment 95 provides the method of any one of Embodiments 1-94, wherein the reoxygenating comprises aerating the denitrified water or sparging of oxygen-containing gas into the denitrified water.

Embodiment 96 provides the method of any one of Embodiments 1-95, wherein the reoxygenating comprises sparging air into the denitrified water.

Embodiment 97 provides the method of any one of Embodiments 1-96, wherein the reoxygenated water has an oxygen concentration of about 1 ppm to about 20 ppm.

Embodiment 98 provides the method of any one of Embodiments 1-97, wherein the reoxygenated water has an oxygen concentration of about 2 ppm to about 8 ppm.

Embodiment 99 provides the method of any one of Embodiments 1-98, further comprising adjusting the pH of the reoxygenated water such that the pH is about 7.

Embodiment 100 provides the method of any one of Embodiments 1-99, further comprising removing or reducing the concentration of one or more gases in the reoxygenated water.

Embodiment 101 provides the method of any one of Embodiments 1-100, further comprising scrubbing from the reoxygenated water hydrogen sulfide, nitrous oxide, nitric oxide, or a combination thereof.

Embodiment 102 provides the method of any one of Embodiments 1-101, further comprising filtering the reoxygenated water.

Embodiment 103 provides the method of any one of Embodiments 1-102, further comprising returning the denitrified and reoxygenated water to the natural environment.

Embodiment 104 provides the method of any one of Embodiments 1-103, wherein the water comprising the water-soluble form of nitrogen, or an unoxidized or unhydrolyzed precursor thereof, is taken from the natural environment.

Embodiment 105 provides the method of any one of Embodiments 104, further comprising returning the denitrified and reoxygenated water to the natural environment downstream of where the water comprising the water-soluble form of nitrogen, or an unoxidized or unhydrolyzed precursor thereof, was taken.

Embodiment 106 provides a method of denitrification of water, the method comprising:
taking water comprising soluble forms of nitrogen from a source, the water comprising a total nitrogen concentration of less than or equal to 20 ppm;

optionally oxidizing or hydrolyzing at least some of the nitrogen to form nitrate;

deoxygenating the water to an oxygen concentration of about 0 ppm to about 0.3 ppm;

exposing the deoxygenated water to denitrifying bacteria immobilized on a porous substrate, the immobilized bacteria cultured from or identical to bacteria native to the area of the natural environment from which the water comprising nitrogen was taken, to convert nitrate in the water to nitrogen gas that is removed and to form a denitrified water; and reoxygenating the denitrified water to an oxygen concentration of about 1 ppm to about 20 ppm;

wherein the denitrified, reoxygenated water has a total nitrogen concentration that is less than the nitrogen concentration of the water from the source and that is about 0.0 ppm to about 2 ppm total nitrogen.

Embodiment 107 provides a method of denitrification of water, the method comprising:

taking water from a natural environment, the water comprising a total nitrogen concentration of greater than 0.8 ppm to equal to or less than or equal to 20 ppm;

optionally oxidizing or hydrolyzing at least some of the nitrogen to form nitrate;

deoxygenating the water to an oxygen concentration of about 0 ppm to about 0.3 ppm;

exposing the deoxygenated water to denitrifying bacteria immobilized on a porous substrate, the immobilized bacteria cultured from or identical to bacteria native to the area of the natural environment from which the water comprising nitrogen was taken, to convert nitrate in the water to nitrogen gas that is removed and to form a denitrified water; and reoxygenating the denitrified water to an oxygen concentration of about 1 ppm to about 20 ppm;

wherein the denitrified, reoxygenated water has a total nitrogen concentration that is about 0.0 ppm to about 0.8 ppm.

Embodiment 108 provides a method of immobilizing or maintaining bacteria on a substrate for denitrification of water, the method comprising:

deoxygenating water comprising a water-soluble form of nitrogen;

exposing the deoxygenated water to denitrifying bacteria on or within a porous substrate to grow or maintain immobilized bacteria on the porous substrate, to convert the water-soluble form of nitrogen in the water to nitrogen gas that is removed, and to form a denitrified water.

Embodiment 109 provides the method of Embodiment 108, wherein the denitrifying bacteria is cultured from or identical to bacteria native to the local environment, to the environment from which the water comprising the water-soluble form of nitrogen or an unoxidized or unhydrolyzed precursor thereof was taken, or a combination thereof.

Embodiment 110 provides a denitrifying bacterial substrate comprising:

a porous substrate; and immobilized bacteria on the substrate, the bacteria cultured from or identical to anaerobic denitrifying bacteria in the local native environment.

Embodiment 111 provides the denitrifying bacterial substrate of Embodiment 109, wherein the bacteria comprise *Pseudomonas stutzeri*, *Pseudomonas denitrificans*, *Pseudomonas aeruginosa*, or a combination thereof.

Embodiment 112 provides the method or the denitrifying bacterial substrate of any one or any combination of Embodiments 1-111 optionally configured such that all elements or options recited are available to use or select from.

What is claimed is:

1. A method of denitrification of water, the method comprising:

deoxygenating water comprising a water-soluble form of nitrogen, the deoxygenation comprising exposing the water comprising the water-soluble form of nitrogen to one or more sulfite compounds in the presence of a metal catalyst comprising iron, the one or more sulfite compounds comprising sodium sulfite, potassium sulfite, sodium bisulfite, sodium metabisulfite, potassium bisulfite, potassium metabisulfite, or a combination thereof;

exposing the deoxygenated water to denitrifying bacteria to convert the water-soluble form of nitrogen in the water to nitrogen gas that is removed and to form a denitrified water, wherein the denitrifying bacteria is immobilized on a porous substrate comprising a ceramic that comprises a vitrification product of a mixture comprising peat; and reoxygenating the denitrified water, wherein the reoxygenated water has a total nitrogen concentration that is less than a total nitrogen concentration of the water comprising the water-soluble form of nitrogen and that is about 0.0 ppm to about 2 ppm total nitrogen.

2. The method of claim 1, further comprising maintaining a concentration of iron in the deoxygenated water exposed to the denitrifying bacteria of about 25 ppb to about 5,000 ppb.

3. The method of claim 1, wherein the reoxygenated water has a nitrate concentration that is about 0.0 ppm to about 2 ppm.

4. The method of claim 1, further comprising oxidizing or hydrolytically converting the nitrogen in the water to form the water comprising the water-soluble form of nitrogen.

5. The method of claim 4, wherein the oxidation or hydrolysis comprises treatment with acid, base, ferrate, ozone, ferric chloride, potassium permanganate, potassium dichromate, potassium chlorate, potassium persulfate, sodium persulfate, perchloric acid, peracetic acid, potassium monopersulfate, hydrogen peroxide, sodium hypochlorite, potassium hypochlorite, or a combination thereof.

6. The method of claim 1, wherein the deoxygenated water has an oxygen concentration of about 0 ppm to about 0.3 ppm.

7. The method of claim 1, wherein the deoxygenating further comprises treating with one or more deoxygenating compounds, heating, exposing to reduced pressure, sparging with a stripping gas, sonicating, contacting with a membrane contactor, or a combination thereof.

8. The method of claim 1, further comprising adding nutrients, food, or a combination thereof, to the water prior to the denitrification.

9. The method of claim 1, further comprising maintaining the immobilized denitrifying bacteria on the porous substrate or growing the immobilized denitrifying bacteria on the porous substrate.

10. The method of claim 1, wherein the denitrifying bacteria is cultured from or identical to bacteria taken from soil in a natural location of the water containing the water-soluble form of nitrogen.

11. The method of claim 1, wherein the denitrifying bacteria comprises *Thiobacillus denitrificans*, *Micrococcus denitrificans*, a *Serratia*, a *Pseudomonas*, an *Achromobacter*, a *alkaligenes*, a *bacillus*, or a combination thereof.

12. The method of claim 1, wherein the denitrifying bacteria is chosen from *Pseudomonas stutzeri, Pseudomonas denitrificans, Pseudomonas aeruginosa*, and combinations thereof.

13. The method of claim 1, wherein the reoxygenating comprises aerating the denitrified water or sparging of oxygen-containing gas into the denitrified water.

14. The method of claim 1, wherein the water comprising the water-soluble form of nitrogen, or an unoxidized or unhydrolyzed precursor thereof, is taken from the natural environment, further comprising returning the denitrified and reoxygenated water to a natural environment.

15. The method of claim 1, the method further comprising:
providing the water comprising the water-soluble form of nitrogen, the providing comprising
taking water comprising a soluble form of nitrogen from a source, the water comprising a total nitrogen concentration of less than or equal to 20 ppm; and
optionally oxidizing or hydrolyzing at least some of the nitrogen to form nitrate;
wherein the reoxygenating comprises reoxygenating the denitrified water to an oxygen concentration of about 1 ppm to about 20 ppm.

16. The method of claim 1, wherein prior to the denitrification and deoxygenation, wherein the porous substrate is a denitrifying bacterial substrate formed using a method comprising deoxygenating water comprising a water-soluble form of nitrogen; and exposing the deoxygenated water to the denitrifying bacteria on or within the porous substrate to grow or maintain immobilized bacteria on the porous substrate, to convert the water-soluble form of nitrogen in the water to nitrogen gas that is removed, and to form a denitrified water.

17. The method of claim 1, wherein the one or more sulfite compounds comprise sodium metabisulfite.

18. A method of denitrification of water, the method comprising:
deoxygenating water comprising a water-soluble form of nitrogen, the deoxygenation comprising exposing the water comprising the water-soluble form of nitrogen to one or more sulfite compounds in the presence of a metal catalyst comprising iron;
exposing the deoxygenated water to denitrifying bacteria to convert the water-soluble form of nitrogen in the water to nitrogen gas that is removed and to form a denitrified water, wherein the denitrifying bacteria is immobilized on a porous substrate comprising a ceramic that comprises a vitrified mixture of a non-clumping clay, dolomitic limestone, CaO, and peat; and
reoxygenating the denitrified water, wherein the reoxygenated water has a total nitrogen concentration that is less than a total nitrogen concentration of the water comprising the water-soluble form of nitrogen and that is about 0.0 ppm to about 2 ppm total nitrogen.

19. A method of denitrification of water, the method comprising:
deoxygenating water comprising a water-soluble form of nitrogen;
exposing the deoxygenated water to denitrifying bacteria to convert the water-soluble form of nitrogen in the water to nitrogen gas that is removed and to form a denitrified water, wherein the denitrifying bacteria is immobilized on a porous substrate comprising a ceramic that comprises a vitrification product of a mixture comprising peat; and
reoxygenating the denitrified water.

* * * * *

UNITED STATES PATENT AND TRADEMARK OFFICE
CERTIFICATE OF CORRECTION

PATENT NO. : 11,795,084 B2  
APPLICATION NO. : 17/267254  
DATED : October 24, 2023  
INVENTOR(S) : Luke et al.

Page 1 of 1

It is certified that error appears in the above-identified patent and that said Letters Patent is hereby corrected as shown below:

In the Specification

In Column 1, Line 9, after "2019", insert --,--

In Column 4, Line 7, delete "5 wt %/o" and insert --5 wt %-- therefor

In Column 7, Line 24, delete "600%," and insert --60%,-- therefor

In Column 10, Line 4, delete "deoxygenation." and insert --reoxygenation.-- therefor In Column 11, Line 41, delete "0.01 wt %/o" and insert --0.01 wt %-- therefor In Column 25, Line 15, delete "ft's" and insert --ft/s-- therefor In the Claims In Column 29, Line 25, in Claim 16, delete "claim 1 ," and insert --claim 1,-- therefor Signed and Sealed this  
Twenty-first Day of January, 2025

Coke Morgan Stewart  
*Acting Director of the United States Patent and Trademark Office*